United States Patent
Cook

Patent Number: 5,816,241
Date of Patent: Oct. 6, 1998

[54] COILED NASAL DILATOR

[76] Inventor: Lori Irene Cook, P.O. Box 1040, Studio City, Calif. 91614

[21] Appl. No.: 767,022

[22] Filed: Dec. 16, 1996

Related U.S. Application Data

[63] Continuation-in-part of Ser. No. 538,031, Sep. 29, 1995, abandoned.

[51] Int. Cl.[6] .......... A61M 15/08; A61M 16/00; A61M 29/00; A62B 7/00
[52] U.S. Cl. .............. 128/200.24; 128/204.12; 606/199
[58] Field of Search .......... 128/204.12, 204.13, 128/206.18, 207.13, 207.18, 200.24, 848; 606/199

[56] References Cited

U.S. PATENT DOCUMENTS

| | | | |
|---|---|---|---|
| D. 310,565 | 9/1990 | Petruson | D24/34 |
| 1,709,740 | 4/1929 | Rogers | 128/204.12 |
| 2,282,681 | 5/1942 | Stotz | 128/206.11 |
| 4,414,977 | 11/1983 | Rezakhany | 128/204.12 |

FOREIGN PATENT DOCUMENTS

| | | | |
|---|---|---|---|
| 24397 | of 1912 | United Kingdom | 128/204.12 |
| 210982 | 2/1924 | United Kingdom | 606/204.45 |
| 768488 | 2/1957 | United Kingdom | 128/204.12 |
| 1244146 | 8/1971 | United Kingdom | 128/204.12 |
| 212601 | 3/1984 | United Kingdom | 128/204.12 |

*Primary Examiner*—Kimberly L. Asher

[57] ABSTRACT

A removable device inserted into the nose which is designed to improve quality of sleep by increasing air-flow volume to lungs and to provide relief from snoring caused by insufficient air and mouth breathing. Triangular in shape with an open-ended base, the device has a tipped vertex and two cone-shaped, spiral coils positioned sideways at the open end of each side, one for each nostril. The device is adjustable by narrowing or widening the span between the coils, by shortening or lengthening the device by rolling or unrolling coils, by changing the direction or slant of the coil to accommodate the configuration of the nostril—which can be moved either from the top of the coil and/or from the bottom of the coil, and by adjusting the depth of the coil by increasing or decreasing the space between the spirals of each coil.

2 Claims, 1 Drawing Sheet

COILED NASAL DILATOR

This application is a Continuation-In-Part of application Ser. No. 08/538,031 filed Sep. 29, 1995, now abandoned.

BACKGROUND OF THE INVENTION

1. Field of Invention

This device, related to the general health or medical device fields, is used to improve the quality of sleep by increasing the volume of air flow into the nostrils and to reduce snoring caused by blocked or semi-blocked air passages.

There are many reasons for breathing problems: Deviated septums, interior scaring, age, accident, or surgery can cause the cartilage to lose some of it firmness and stability. Perhaps even the wearing of glasses can contribute to this condition. The narrowest part of the nose, called the ostium internum, located behind the nostril flare—the ala, is also the location of the nasal air passages to the lungs. When the lateral wall of the vestibule (immediately inside the entrance to the nostril) in the area of the ostium internum loses its firmness, the tissue becomes loose and draws inward with each inhalation of breath, thus effectively blocking off the air supply. The reverse is true with each exhalation, ie., the tissue is expanded outward. In an effort to improve the air supply, a person will adjust his head and/or body position many times during the night and is often aware of a slight awakening which prevents the deep sleep required for REM (Rapid Eye Movement),the dream state—the deepest state of sleep. Without this REM state of sleep, sleep deprivation follows, leading to chronic fatigue and a sense of being tired even upon waking in the morning. Many sleepers simply give up and resort to mouth breathing, which leads to a whole new set of problems, the least of which is not increased snoring and dry mouth. Long periods of mouth breathing can lead to dental problems and increased interruption of sleep.

The medical profession has addressed the problem by operating upon those with deviated septums, which does not always correct the condition. Other devices have been tried, with little success it would seem, since none of the insertion devices is readily available.

2. Description of the Prior Art

Referring to the prior art, disclosures are of different concepts and have no relationship to the present nose device, except to say that they are all nose devices. One prior disclosure is an exterior device whose major purpose is to act as an inhaler for medication, while another disclosure cannot really be addressed since only drawings were sent. It appears to be based upon some kind of spring capability.

Yet another disclosure, although a dilator, as is the present device, is in no way adjustable by the consumer and due to its general contour and the moist nature of the inside of the nose, it is unlikely that this device would be able to stay in place. The bowing of the unit would actually encourage its slipping out.

Another prior disclosure, referred to as "Breeze" in correspondence is unlike the present device as to material, shape and concept. Tempered stainless steel can be flexible but it does not have the malleability of copper wire. The shape of the Breeze patent has little relationship to the triangle shape of this applicant's device; but the greatest difference is in the coil. The Breeze coil is a front-on coil, elongated, with each revolution of the coil the same size. The coil enters and stays in the center of the nostril, whereas, the present device has the coils entering the nose in a sideways fashion and they are used to support and lift the tissue at the point where the nasal blockage occurs. The coil is also cone-shaped and sightly elliptical. Furthermore, the Breeze device is not adjustable, whereas, the fine tuning provided by this applicant's invention provides for individual sizes and shapes of noses which are inherent in the basic concept of the device, and which the consumer, himself, can adjust.

It is doubtful if the Breeze invention would ever remain in place. There is no way to get traction which must be present if the device is to remain where it is placed. Since human nostrils are more or less parallel to the vertical line of the body (depending upon the position of the head) gravity is a force which must be taken into account and is the reason why most nose devices do not work: They will not remain in place. Even when a user is lying down, with head upon a pillow there is still a downward direction of the appliance. Add to that, the turning of the body and/or head during sleep and dislodging occurs. For those persons who sleep on their stomach, turning the head to the other side means facial contact with the pillow, which in itself causes displacement of a nose appliance. However, with the present triangular device in apposition to the triangularity of the nose, with the unique placement of the coils and with the ability to spread the device, thus creating tension, there are three methods of achieving traction which is the major accomplishment of this device: When it is put into place correctly, it stays where it is placed as long as it is worn only during sleep or during periods of inactivity.

Also, a further prior disclosure, in part, nasal distender and in part, medicine dispenser, has a different concept, having a U-shaped configuration rather than coils and is also non-adjustable, other than width.

Other disclosures are for medical purposes—one shaped as a FIG. 8 filter against dust and pollens; and another as a dispenser of medicine or as a filter meant to be cast from a mold and, therefore, not adjustable. Its shape, nothing like the present device, resembles a football helmet. Neither one has enough characteristics in common with the present devise to warrant further comment.

Another disclosure, referred to as "Warburton" is quite different:

(1) The coils of the present device are conical in shape, which provide for more contact with the interior of the nostril, thus contributing to maintaining placement through a distribution of weight along all of the spirals.

The Warburton coil is flat.

(2) The present device provides more comfort within the nose. Since the flare of the nostril is essentially conical in shape, this conical shape of the device contributes to comfort by the use of this weight distribution.

The flat surface of the Warburton coil, with all of the weight of the nose confined to one arc, produces discomfort.

(3) The vertex or tip of the present device is tipped upward for better fit, leaving the tensile energy intact, since the tip is on a different plane.

By creating a circular tip on the same plane as the sides, the amount of tension generated by the Warburton is somewhat dissipated by traveling around the circular tip before it travels along the sides. Furthermore, when the coil begins, there is another abrupt, higher level of line upward as the curve of the coil begins. At this point most tensile energy is lost.

(4) The shanks or lines of the sides of the present device are linear which produce greater tension within the device as they relate to the spring action at the point of the coil.

(5) The present device is designed for the coils to rest along the bottom of the nose vestibule while the upper spirals of the coil rest along the inside UPPER flare of the nostril; the sides and tip of the device run along the UPPER portion of the nose, with the tipped Vertex straddling the UPPER region above the columella. Once the user has adjusted to the sensation of "nostril flare," there is no longer awareness of the device being worn.

In the case of the Warburton, the unit is designed to rest on the BOTTOM of the nose vestibule and across the BOTTOM of the columella where it is more vulnerable to displacement and since it is in contact with the skin, the user also has an awareness that the unit is there, due to inevitable mouth movement.

It is also this mouth movement which helps to displace the unit while being worn. Another displacement factor is the single line or one-track effect of the unit, coupled with the moist interior of the nose, allowing the unit to easily slide out of the nose.

SUMMARY OF THE INVENTION

This removable nasal device can be inserted into the nose before sleep in order to increase the volume of air flow into the lungs, thus improving the quality of sleep and to reduce snoring caused by lack of air which often results in mouth breathing. Made of copper wire in tension, or any material which has similar tensile strength, flexibility and malleability, the device is triangular in shape with a tipped vertex, an open base, and a cone-shaped spiral, slightly elliptical, alongside the end of each of the two sides. The device is meant to benefit those who suffer from restricted air flow into the nasal passages due to shape or condition of the interior nostril areas and their cartilage support system, including deviated septums. The device can also be worn during periods of inactivity.

BRIEF DESCRIPTION OF THE DRAWINGS

The features of the present invention which are believed to be novel are set forth with particularity in the appended claims. The present invention, both as to its organization and manner of operation, together with further objects and advantages thereof, may best be understood with reference to the following description, taken in connection with the accompanying drawings in which:

DETAILED DESCRIPTION OF THE PREFERRED EMBODIMENT

The present device is simple but effective and is completely adjustable in order to accommodate the various shapes and sizes of noses. Constructed of flexible material and shaped as a nearly equilateral triangle, it consists of a single vertex (curved rather than pointed, and tipped upward) with left and right shanks, and two conical coils. The base of the triangle is open-ended with a coil at each of the two ends, located alongside each end of the shank. Each coil is a cone-shaped spiral constructed to allow air to pass through, consisting of revolutions, the number of which can be increased or decreased in order to provide for differences in nose sizes.

The coil stands against the lateral wall near the ostium internum in each nostril, gently expanding the neck-like area where the air blockage takes place near the opening of the nasal passages. The device is easily inserted and when adjusted properly, the user is not aware of its presence. When in place, the only part visible is the tip of the vertex which lies above the upper area of the columella, the exterior vertical division between the two nostrils.

Upon placement, the wearer is immediately aware of greatly increased breathing capacity. This acts as an inducement to fall asleep and improves the quality of sleep immeasurably since one no longer wakes in a struggle for breath. It also acts as an aid in correcting snoring caused by mouth breathing.

Adjustments are made by:

1. Widening or narrowing the span of the open ends to accommodate the width of the nose.

2. Slanting coils toward lateral wall of nose by pulling out top coil directly under shank to accommodate the nostril flare, called the ala.

3. Slanting coils away from the lateral walls by pushing bottom coil inward, also to accommodate to the shape of the nostril.

4. Shortening—rolling up coils in small increments for desired length.

5. Lengthening—unrolling coils in small increments.

6. Adjusting depth of coil by decreasing the space between the spirals of the coils; or increasing the depth by increasing the space between the spirals.

All of the above adjustments can also accommodate the differences between nostrils since there are few perfectly symmetrical noses.

The device is held in place by (1) the tensile strength of the material used, (2) by the span of the device (the width between the coils) and (3) by the triangularity of the device in apposition to the triangle shape of the nose.

The device provides individually for each nostril, the coils serving as retaining walls to push aside and lift the tissue at the point where the nose narrows—at the ostium internum.

The following measurements are guidelines and can be adjusted as required. Adjustments inherent in design also add refinement to fit.

Length of material:

Small, Medium, Large sizes: 10.2 cm to 18.2 cm

Size of Coils: (Coils are mirror copies of each other)

Small, Medium, Large: 8 mm to 12 mm

Figure 1:
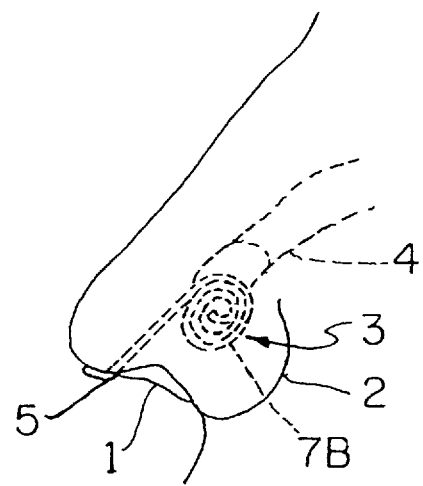
FIG. 1 is a profile view illustrating the Device in place, the coils resting on edge against the flare of the ala near the ostium internum and the nasal passages. This view also illustrates the snug fit of the Vertex above the top of the columella.

FIG. 1. (1) Profile of Nose with Columella, the exterior tissue which divides the nostrils; (2) The flare of the nostril called the Ala; (3) Placement of the Device within a nose; (4) Nasal Cavity—air passage to the lungs; (5) Vertex of Device across top of Columella with the (6B) Right Shank shown in dotted line; (7B) Position of Right Coil (shown in dotted line) near rear edge of Ala.

Figure 2:
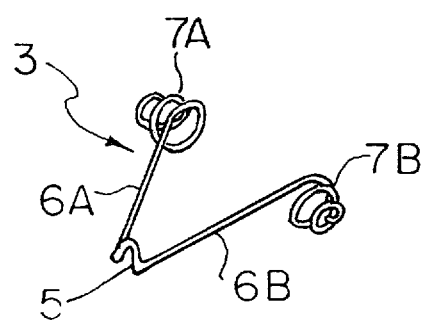
FIG. 2 shows The Device with the tipped vertex which fits snugly around the tip of the nose above the columella; the two shanks, each ending in sightly elliptical, cone-shaped, spiraled coils which rest along side the ala near the nasal passage in each nostril.

FIG. 2. 3-dimensional Overhead Frontal View of Device with upward-tipped Vertex; (5) Vertex; (6A & B) Left and Right Shanks; (7A & B) Left and Right Coils.

The shanks enter the nostrils in the upper position, above the coils. Each coil is sized according to need as determined by size of nostrils. The cone-shaped spirals are designed to allow the maximum amount of air to pass through them, rather than acting as an impediment to breath. The shape of the coils also act as retaining walls to lift and push back any tissue which obstructs the air passages and are controlled by the spread of the shanks and by the natural tensile strength of the material used in the manufacture of the Device. The slightly elliptical spiraled coils are cone-shaped with the smallest coil the most prominently placed into the natural flare of the ala, with each succeeding revolution of the spiral larger than the one proceeding it. This configuration displaces the weight load from one point to all of the surfaces of the spirals having contact with tissue and contributes to the Device's comfort when worn.

The triangle shape of the Device in apposition to the triangularity of the nose, added to the tensile strength of the Device and the positioning of the coils, force the widening of the tissue at the point of the Ostium Internum, thus allowing the maximum amount of air to enter the nasal passages and pass on down into the lungs.

While particular embodiments of the present invention have been shown and described, it will be obvious to those skilled in the art, that changes and modifications may be made without departing from this invention its broader aspects and, therefore, the aim in the appended claims is to cover all such changes and modifications as fall within the true spirit and scope of this invention.

I claim:

1. A nasal device adapted for insertion into the vestibule of the nose to push aside and lift nasal tissue for providing unobstructed air passages into the lungs in order to improve the quality of sleep and to inhibit snoring, comprising:

(a) a triangularly shaped unit constructed of material which has tensile strength and malleability, consisting of a vertex, and left and right sides, each side ending in an elliptical, cone-shaped, spiral coil which is adapted to rest sideways near the ostium internum, the narrowest part of the nose and the site of air blockage due to deviated septum or infirm tissue which draws inward with each inhalation of breath causing an insufficient air supply, snoring, mouth breathing and poor quality of sleep;

(b) means for retaining said triangularly shaped unit in position in a wearer's nose comprising a snug fit of said vertex across the columella of the nose and the tensile strength of the material of said unit, said triangularly shaped unit being inserted in apposition to the triangularity of the nose with said coils serving as paddles to lift and restrain tissue away from nasal air passages;

(c) said coil construction displacing pressure from one point to all surfaces of said coils that come into contact with the nasal tissue, such construction being largely responsible for increasing a wearer's comfort and as an aid in maintaining placement of said device within a nose of a wearer;

(d) said vertex being tipped upward with respect to said left and said right sides, with said left and said right sides having a linear length.

2. The device of claim 1, wherein said device is adjustable by the wearer for customizing for a particular nose by:

a. widening or narrowing a span of the device, b. slanting a top and/or a bottom of said coil toward the ala of the nose, c. slanting the top and/or the bottom of said coil away from the ala of the nose, d. shortening of said coils by rolling up said coils in increments for desired length, e. lengthening of said coils by unrolling said coils in small increments, f. increasing or decreasing depth of each coil by adjusting spaces between spirals of each said coil.

* * * * *